United States Patent [19]

Yoshizumi et al.

[11] Patent Number: 4,514,496

[45] Date of Patent: Apr. 30, 1985

[54] PROCESS FOR PRODUCING ALCOHOL BY FERMENTATION WITHOUT COOKING

[75] Inventors: Hajime Yoshizumi, Takatsuki; Nobuya Matsumoto; Osamu Fukuda, both of Ibaraki; Osamu Fukushi, Usuki, all of Japan

[73] Assignee: Suntory Limited, Osaka, Japan

[21] Appl. No.: 562,995

[22] Filed: Dec. 16, 1983

Related U.S. Application Data

[63] Continuation of Ser. No. 326,283, Dec. 1, 1981, abandoned.

[30] Foreign Application Priority Data

Dec. 16, 1980 [JP] Japan ................. 55-178523
May 7, 1981 [JP] Japan ................. 56-68974
May 28, 1981 [JP] Japan ................. 56-82217
Jun. 1, 1981 [JP] Japan ................. 56-84823

[51] Int. Cl.³ .................. C12P 7/06; C12P 7/14; C12C 7/00; C12G 3/00
[52] U.S. Cl. .................. 435/162; 426/13; 426/16; 426/29; 435/161
[58] Field of Search ........... 435/161, 162; 426/13, 426/16, 29

[56] References Cited

U.S. PATENT DOCUMENTS

| | | | |
|---|---|---|---|
| 3,345,179 | 10/1967 | Pollock et al. ............... | 426/16 |
| 3,988,204 | 10/1976 | Andreasen et al. ........... | 426/29 X |
| 4,092,434 | 5/1978 | Yoshizumi et al. ........... | 426/29 X |
| 4,140,799 | 2/1979 | Nagodawithana et al. ... | 426/29 X |

FOREIGN PATENT DOCUMENTS 880875 9/1971 Canada .................. 426/29

OTHER PUBLICATIONS

De Clerck, J., A Textbook of Brewing, vol. one, Chapmant Hall, Ltd. London, 1957, (pp. 275-276).

*Primary Examiner*—David M. Naff
*Attorney, Agent, or Firm*—Frishauf, Holtz, Goodman & Woodward

[57] ABSTRACT

Alcohol is produced in a noncooking system by mixing a ground starchy material with mashing liquor at the range that the weight ratio of mashing liquor to ground starchy material is from 1.8 to 3.4 to form a slurry, without cooking, adding to the slurry at least 3.5 units as a saccharifying power of the enzyme preparation derived from a microorganism source, favorably Rhizopus sp., as a saccharifying agent, further adding an alcoholic fermenting yeast, and fermenting the slurry. Examples of the starchy material are cereals such as maize, sorghum, wheat, barley, rye, rice, barnyard millet, German millet, and common millet, and starchy rootcrops such as sweet potato and cassava.

34 Claims, No Drawings

PROCESS FOR PRODUCING ALCOHOL BY FERMENTATION WITHOUT COOKING

This application is a continuation of application Ser. No. 326,283, filed Dec. 1, 1981, abandoned.

BACKGROUND OF THE INVENTION

1. Field of the Invention

This invention relates to a process for producing alcohol by saccharification and fermentation of a starchy material without cooking.

2. Description of the Prior Art

It is the conventional practice to cook a mash consisting of a slurry of a ground starchy material at high temperatures such as 150° C. [*Industrial Fermentation* Vol.1, ed by L. A. Underkofler and R. J. Hickey, Chemical Publishing Co., Inc., 1954. p.17., *Trans Am. Inst. Chem. Eng.*, 40, 421 (1944), *Food Can.*, 29, 23 (1969)] The purpose of cooking is to rupture the structure of the raw material grits thereby eluting starch from the grits to avoid a viscosity increase owing to gelatinization after eluting, aid in the actions of liquefying and saccharifying enzymes, and further to kill microorganisms harmful to saccharification and fermentation. After cooking, however, the mash must be cooled to about 25° to 35° C. which is the fermenting temperature, and the energy required for cooling is great. Hence, the total energy consumption including the energy spent for cooking is enormous in the conventional high temperature cooking process.

In recent years, the aggravated supply of energy caused by the increased price of petroleum has prompted much research work for development of new energy sources. In particular, much interest has been aroused in ethanol which can be renewably produced from biomass resources grown under the action of solar energy because it is expected to be a petroleum fuel substitute.

Some of the present inventors previously developed an energy-saving process for producing alcohol which involves cooking at a temperature of 75° to 85° C. (U.S. Pat. No. 4,092,434 issued May 30, 1978, G.B. Pat. No. 1,503,760 issued Mar. 15, 1978).

It is known on the other hand the processes for Japanese sake brewing and alcoholic production without cooking. [1. *J. Ferm. Ass. Japan* 10 319 (1952), 2. *J. Ferm. Ass. Japan* 21 83 (1963), 3. *J. Ferment. Technol.* 58 237 (1980), 4. *J. Brew. Soc. Japan* 75 858 (1980), 5. Abstract of Papers, Annual Meeting of the Society of Fermentation Technology of Japan, Osaka, November 1980 P4]. However, these techniques require some special operations such as acidification of mash (pH 3.5), which prevents contamination of harmful microorganisms (above-cited 1, 2, 3, 4). And the prior techniques require a longer period of the time for the saccharification and fermentation (above-cited 1, 2, 4, 5) or such prior techniques require complex process steps such as dialysis of a fermented broth (above-cited 3, 4) and are difficult to be accepted industrially.

SUMMARY OF THE INVENTION

The present inventors have further investigated the process of the above-cited U.S. Pat. No. 4,092,434, G.B. Pat. No. 1,503,760 and now arrived at a novel energy-saving process for producing alcohol from starchy materials which requires no cooking steps.

According to this invention, there is provided a process for producing alcohol, which comprises mixing a ground starchy material with mashing liquor, at the range that the weight ratio of mashing liquor to ground starchy material is from 1.8 to 3.4 to form a slurry, without cooking the slurry, without adjusting the pH of the slurry, adding to the slurry a saccharifying enzyme preparation derived from a microorganism source, or malt, or both as a saccharifying agent in an amount of at least 3.5 units of saccharifying titer per one gram of raw material on wet basis (the saccharifying activity determined in accordance with JIS K-7001) on using the enzyme or the mixture of the enzyme and malt or at least 10 units as saccharifying titer on using malt only in terms of an enzyme titer and further mixing an alcoholic fermenting yeast; and then fermenting the slurry.

DETAILED DESCRIPTION OF THE INVENTION

In the conventional industrial process, the weight ratio of the raw material vs mashing liquor is from 1:4.3 to 1:2.8, but in the process of this invention, the concentration of the raw material in the slurry is relatively high. Furthermore, it is favorable that in the initial stage, fermentation is carried out by maintaining the yeast concentration about $2 \times 10^7$ cells/ml mash. In the conventional process, the final concentration of the resulting alcohol in the mash is about 11%, whereas it is about 15% in the process of this invention.

The process of the present invention is based on the surprising discovery that by adopting a relatively high mash concentration, a high fermentation yield and about 40% higher final alcohol concentration in the mash than in the conventional process can be obtained without cooking and any special pH adjustment.

The term "without cooking" or "noncooking", as used herein, means that no heat-treatment is carried out which will result in an increase in the viscosity of the slurry of the starchy material. In other words, this means that the raw material slurry is not treated at a temperature at which starch is converted to α-starch or gelatinized. The temperature at which the viscosity increase begins differs depending upon the raw material and its concentration. Table 1 summarizes the relation between the initial concentration of a raw material and the starting temperature to increase the viscosity examined with regard to ground whole kernels of maize and corn starch by means of an amylograph of HAAKE. INC.. Thus, for example, when the weight ratio of the ground whole kernels of maize vs mashing water is 1:1.8, the slurry should be prepared without increasing viscosity due to gelatinization at a temperature lower than 55.8° C., and when the weight ratio of corn starch vs mashing water is 1:3.4, the slurry should be prepared at a temperature of less than 66.5° C.

TABLE 1

| Ground maize: water (by weight) | 1:3.4 | 1:2.9 | 1:2.4 | 1:2.1 | 1:1.8 |
|---|---|---|---|---|---|
| Temperature of viscosity increase | 66.5° C. | 63.8° C. | 60.0° C. | 57.5° C. | 55.8° C. |
| Corn starch: water (by weight) | 1:3.4 | 1:2.9 | 1:2.4 | 1:2.1 | 1:1.8 |
| Tempera- | 66.5° C. | 66.5° C. | 65.0° C. | 64.0° C. | 62.0° C. |

TABLE 1-continued ture of
viscosity
increase

In a noncooking system, contamination by noxious microorganisms is likely to reduce the yield of fermentation or to stop the fermentation. However, according to the present invention, the concentration of fermentable sugars in the mash is enough but not excessive to the yeast fermentation. It seems that such the low concentration of sugars in the mash does not affect the saccharifying reaction by feedback inhibition.

Consequently, the process of the invention does not provide conditions suitable for the growth of noxious microorganisms such as spoilage bacteria, because of the shortage of assimilable sugars as a carbon source for the growth of bacteria, and there is scarcely any likelihood of contamination by the noxious microorganisms.

Furthermore, the process of the invention can save on energy for cooking, and is advantageous in regard to energy balance over conventional processes directed to the production of fuel alcohols from starchy materials.

Another advantage is that since the solids in the mash after fermentation have not experienced a heat history, they are easy to filter off, and can be separated by a simple filtration or decantation operation.

The process of this invention is described below in detail.

PREPARATION OF THE STARTING RAW MATERIAL

Examples of the starchy raw material used in this invention include cereals such as maize, sorghum, barley, wheat, rice, barnyard millet, German millet and common millet starchy rootcrops such as sweet potato and cassava, and raw starches separated from these materials.

The starting raw material may be a mixture of such materials. The cereals are used as ground whole kernels, or ground products of whole kernels from which the germ portion has been removed. The starchy rootcrops are used as ground products obtained from either raw starchy materials or from dried starchy materials. The particle diameter of the raw material should better be as fine as possible. Usually, it is sufficient that at least 30% of the starchy material has a particle size of not more than 840 μm.

PREPARATION OF THE SLURRY

The ground raw material is mixed with mashing liquor at a weight ratio (ground raw material:mashing liquor) on wet basis of from 1:3.4 to 1:1.8 to form a slurry. Mashing liquor may be water or a mixture of water and a distillation residue of the mash which is known as "stillage" or stillage only.

If the concentration of the raw material in the slurry is lower than the above-specified limit (1:3.4), fermentation does not smoothly proceed. If it is higher than the above-specified limit (1:1.8), both the efficiency of saccharification and the yield of fermentation decrease. It is essential that the concentration of the raw material in the slurry should be within the above-specified range.

Use of stillage resulting from distilling off of alcohol from the mash after fermentation, in combination with water, is preferred because sugars, nitrogen, phosphorus, and other nutrients remaining in the stillage can be utilized, and the use of stillage increases the buffering ability.

The stillage may be the one obtained by distilling off alcohol from the fermented mash by ordinary distillation under heat, or the one obtained by further removing crude solids from the above-mentioned type of stillage. The latter type is preferred, however.

Use of stillage together with water has been practiced heretofore, but the amount of stillage in the prior art is only up to 50% of the total amount of mashing liquor.

It is known that the fermentation residue left after distilling off alcohol by vacuum distilling is directly used as a raw material in the next cycle of alcoholic fermentation (Japanese Laid-Open Patent Publication No. 15691/1981). This method, however, requires a special operation and is not so easy to operate.

Since the process of this invention includes no cooking system, the viscosity of the slurry is low. Hence, the use of stillage in an increased proportion does not reduce the efficiency of transportation of the mash. Because of these advantages, the stillage can be used in a proportion of 50 to 100% instead of mashing water in the process of this invention.

The use of such a large amount of stillage produces an effect of facilitating the activation of yeast, particularly in the early stage of fermentation, promoting vigorous fermentation, and bring about good fermentation results.

The saccharifying agent to be added to the slurry is a saccharifying enzyme preparation derived from a microorganism source, or malt, or both. The amount of the saccharifying enzyme preparation is at least 3.5 units/g of the raw material on wet basis in terms of an enzyme titer. When malt is used, its amount is included in the amount of the raw material. Moreover, when malt is used as the sole saccharifying agent, the amount of malt is necessary to be equivalent at least 10 units/g as titer.

Existing and commercially available enzyme preparations can be used as the saccharifying enzyme preparations derived from microorganism source. They may be either the ones present in microorganism culture broths, or the ones extracted from the culture broths. For example, saccharifying agents derived from microorganism of the genus Aspergillus and Rhizopus are known to decompose raw starch, and are useful as the saccharifying agent in this invention. Particularly, enzyme preparations derived from Rhizopus sp. are suitable for the practice of the present invention because the pH of the slurry in this invention is 4.0 to 5.0 with an average of 4.6, and they have higher activity on saccharification of raw starch than those derived from Aspergillus sp. and exhibit strong saccharifying power.

The saccarifying activity of the enzyme preparations derived from microorganisms is expressed in terms of an enzyme titer measured in accordance with the method of JIS K-7001.

On the other hand, one unit of saccharifying power of malt is defined as the activity equivalent to produce 10 mg of maltose for 10 minutes at 40° C. from 1% soluble starch (pH 4.5).

In the present invention, the pH of the mash during fermentation is usually 4.0 to 5.0 with an average of about 4.5. On the other hand, the optimal pH for raw starch decomposition by malt is about 4.6. Accordingly, enzymes in the malt which participate in the decomposition of raw starch act in the vicinity of the optimal pH of malt.

SACCARIFICATION AND FERMENTATION

Usual alcohol fermenting yeasts can fully maintain their activities at a mash pH of 4.0 to 5.0. Accordingly, in the process of this invention, saccharification of starch is not retarded and alcoholic fermentation proceeds rapidly in spite of the fact that the starch is not converted to α-starch nor gelatinized. This fact is one of the important points which the present inventors discovered.

The yeast starter used is a yeast cultivated in a conventional manner, and the amount of the yeast mixed to the slurry should be at least $2 \times 10^6$ cells/ml of the mash as the initial yeast population. In an especially preferred embodiment, for a period of at least 10 hours from the starting time when the raw material slurry is combined with yeast starter, the yeast population is always maintained to at least $2 \times 10^7$ cells/ml of the mash. The method of achieving this is to add $2 \times 10^7$ (cells/ml of mash) of yeast to the slurry, or to mix the yeast starter to a part of the slurry and after the yeast has grown, gradually add the remaining slurry. The latter method is preferred from the operational view point. By this operation, vigorous fermentation is carried out as soon as the raw material slurry is combined with yeast starter. Since alcoholic fermentation proceeds vigorously by the yeast, noxious microorganisms scarcely proliferate despite the absence of a cooking step, and contamination by spoilage microorganisms does not occur. The mash vigorously moves in a convectional manner. This convectional phenomenon causes uniformity of the density of the yeast and other components to provide preferred saccharifying and fermenting conditions. Specifically, eluting of starch from the ground raw materials is promoted. By these synergistic effects, fermentation yields equivalent to, or higher than, those in the conventional processes can be obtained within nearly the same periods of time as the conventional process by the noncooking process of the invention.

In some cases, for example depending upon the shape of the fermenter tank, the convection of the mash may be effected forcibly. If a raw material markedly contaminated by bacteria is used, the process of the invention may be carried out in the presence less than 320 ppm of sulfur dioxide. As mentioned above, the present invention is simple and economic method and the final concentration of the resulting alcohol in the mash is high such as 15% or over. Consequently, pure alcohol can be economically produced by conventional distillations.

The following examples illustrate the present invention more specifically.

SACCHARIFYING ENZYME PREPARATIONS

Tables 2 shows the analysis of various saccharifying enzyme preparations from microorganisms.

TABLE 2

| | Preparation code | | | | |
|---|---|---|---|---|---|
| | A | B | C | D | E |
| | | | Origin of enzyme | | |
| | Rhiz. sp.* (No. 204) | Rhiz. sp.* (No. 202) | Rhiz. sp.* (No. 212) + Asp. sp.* (No. 107) | Asp. sp.* (No. 186) | Asp. sp.* (No. 171) |
| Liquefying power | 105 U/g** | 1850 | 103 U/g** | 45 U/g** | 118 U/g** |
| Dextrinizing power | 400 | 5285 | 286 | 5347 | 588 |
| Saccharifying power | 2503 | 2236 | 1764 | 745 | 3763 |
| Protease | | | | | |
| (acid) | 985 | 3761 | 555 | 1236 | 13694 |
| (neutral) | 269 | 1262 | 1074 | N.D.*** | 1969 |
| (alkaline) | trace | 1080 | trace | N.D.*** | 1050 |
| Cellulase | 8.9 | 563 | 2.6 | 3.2 | 3.2 |
| Pectinase | 62 | 93 | 48 | 21 | 64 |

*Rhiz. sp.: Rhizopus sp.
Asp. sp.: Aspergillus sp.
**U: short for Units
***N.D.: Not detected Enzyme preparation (1 g) was added to distilled water (1000 ml) and then occasionally stirred for 1 hour at 30° C. The supernatant obtained by centrifugation (3000 r.p.m., 10 min.) was used as enzyme solution. Liquefying power, dextrinizing power, saccharifying power, protease, cellulase and pectinase were assayed by the methods of Wohlgemuth modified, Tsujisaka, JIS K 7001, Kunitz, Miller, and Willstatter-Schudel, respectively.

Table 3 shows the analysis of malts.

TABLE 3

| Malt No. | A | B | C |
|---|---|---|---|
| Moisture (%) | 4.5 | 4.2 | 4.6 |
| Extract | | | |
| fine (%) | 76.6 | 80.1 | 77.1 |
| Coarse (%) | 75.4 | 79.4 | 76.4 |
| pH of wort | 5.9 | 5.7 | 5.9 |
| Saccharifying power (U/g) | 46 | 110 | 113 |

Ground malt (1 g) was added to distilled water (1000 ml) and then occasionally stirred for 1 hour at 30° C. The supernatant obtained by centrifugation (3000 r.p.m., 10 min.) was used as enzyme solution. Saccharifying power was assayed by the method of JIS K 7001. One unit of saccharifying enzyme (amylase) is defined as the activity equivalent to produce 10 mg of maltose for 10 min. at 40° C. from 1% soluble starch (pH 4.5).

PREPARATION OF SAMPLES

Starchy raw materials were ground in a dry condition and used for analysis. The degrees of grinding were as follows: The sweet potato and cassava used as raw materials were dried materials.

TABLE 4

| Raw material | Particle size(*) | A (%) | B (%) | C (%) | D (%) | E (%) | F (%) | G (%) |
|---|---|---|---|---|---|---|---|---|
| Maize | above 840 μm | 69.0 | 28.8 | 21.6 | 20.8 | 10.2 | 4.4 | 0 |
| | 420–840 μm | 16.5 | 35.3 | 38.0 | 37.1 | 35.5 | 36.7 | 14.5 |
| | 250–420 μm | 5.8 | 10.8 | 10.9 | 10.9 | 12.6 | 12.3 | 11.9 |
| | 177–250 μm | 2.2 | 10.7 | 8.1 | 5.5 | 4.7 | 5.0 | 5.7 |
| | 149–177 μm | 1.9 | 3.6 | 4.5 | 1.2 | 0.3 | 1.1 | 1.3 |
| | below 149 μm | 4.6 | 10.8 | 16.9 | 24.5 | 36.7 | 40.5 | 66.6 |
| Sorghum | Above 840 μm | 69.2 | 29.0 | 21.5 | 20.2 | 11.0 | 4.0 | 0 |
| | 420–840 μm | 16.3 | 34.8 | 37.6 | 37.5 | 35.3 | 36.5 | 14.2 |
| | 250–420 μm | 6.0 | 11.0 | 10.8 | 11.2 | 12.0 | 11.8 | 11.5 |
| | 177–250 μm | 2.5 | 11.0 | 8.5 | 6.5 | 6.3 | 3.0 | 6.1 |
| | 149–177 μm | 2.0 | 3.8 | 4.7 | 1.8 | 1.0 | 1.2 | 1.7 |
| | below 149 μm | 4.4 | 10.9 | 16.4 | 23.4 | 35.0 | 41.5 | 67.6 |
| Barley | above 840 μm | 67.5 | 30.5 | 20.0 | 19.1 | 9.1 | 3.7 | 0 |
| | 420–840 μm | 16.0 | 36.5 | 39.1 | 36.0 | 34.8 | 32.0 | 17.5 |
| | 250–420 μm | 6.0 | 9.0 | 11.0 | 12.5 | 13.7 | 13.5 | 12.0 |
| | 177–250 μm | 2.1 | 10.5 | 9.0 | 5.9 | 5.7 | 5.0 | 5.0 |
| | 149–177 μm | 3.0 | 3.5 | 5.0 | 1.5 | 1.2 | 1.8 | 1.6 |
| | below 149 μm | 5.0 | 9.5 | 16.4 | 24.4 | 34.9 | 42.0 | 62.8 |
| Wheat | above 840 μm | 68.5 | | | | 9.8 | | |
| | 420–840 μm | 14.8 | | | | 35.0 | | |
| | 250–420 μm | 6.5 | | | | 13.0 | | |
| | 177–250 μm | 1.9 | | | | 5.2 | | |
| | 149–177 μm | 2.5 | | | | 1.3 | | |
| | below 149 μm | 5.8 | | | | 35.7 | | |
| Rye | above 840 μm | 69.5 | | | | 7.8 | | |
| | 420–840 μm | 16.3 | | | | 34.2 | | |
| | 250–420 μm | 5.5 | | | | 13.5 | | |
| | 177–250 μm | 2.1 | | | | 5.2 | | |
| | 149–177 μm | 2.0 | | | | 1.1 | | |
| | below 149 μm | 4.6 | | | | 38.2 | | |
| Rice | above 840 μm | 69.5 | | 20.5 | | 10.0 | | 0 |
| | 420–840 μm | 16.5 | | 38.4 | | 36.4 | | 13.0 |
| | 250–420 μm | 5.2 | | 12.1 | | 12.3 | | 11.5 |
| | 177–250 μm | 2.0 | | 6.5 | | 4.0 | | 6.3 |
| | 149–177 μm | 2.0 | | 4.1 | | 1.1 | | 1.5 |
| | below 149 μm | 4.8 | | 18.1 | | 36.2 | | 67.7 |
| German millet | above 840 μm | | 32.5 | | | 11.0 | | |
| | 420–840 μm | | 37.0 | | | 34.4 | | |
| | 250–420 μm | | 13.2 | | | 12.0 | | |
| | 177–250 μm | | 6.7 | | | 5.0 | | |
| | 149–177 μm | | 2.0 | | | 1.0 | | |
| | below 149 μm | | 8.6 | | | 36.6 | | |
| Barnyard millet | above 840 μm | | 30.5 | | | 10.0 | | |
| | 420–840 μm | | 36.1 | | | 36.0 | | |
| | 250–420 μm | | 9.8 | | | 13.0 | | |
| | 177–250 μm | | 10.0 | | | 4.0 | | |
| | 149–177 μm | | 4.0 | | | 1.8 | | |
| | below 149 μm | | 9.6 | | | 35.2 | | |
| Common millet | above 840 μm | | 31.5 | | | 9.8 | | |
| | 420–840 μm | | 38.0 | | | 37.5 | | |
| | 250–420 μm | | 12.5 | | | 11.8 | | |
| | 177–250 μm | | 7.1 | | | 5.7 | | |
| | 149–177 μm | | 3.0 | | | 1.8 | | |
| | below 149 μm | | 7.9 | | | 33.4 | | |
| Cassava | above 840 μm | | 38.4 | | 19.4 | 10.6 | | |
| | 420–840 μm | | 32.5 | | 42.9 | 39.8 | | |
| | 250–420 μm | | 12.1 | | 17.9 | 23.6 | | |
| | 177–250 μm | | 8.2 | | 10.6 | 13.6 | | |
| | 149–177 μm | | 3.2 | | 2.7 | 4.8 | | |
| | below 149 μm | | 5.6 | | 6.5 | 7.6 | | |
| Sweet potato (dried chips) | above 840 μm | | 32.5 | | | 9.0 | | |
| | 420–840 μm | | 34.0 | | | 32.5 | | |
| | 250–420 μm | | 13.0 | | | 10.2 | | |
| | 177–250 μm | | 10.2 | | | 3.8 | | |
| | 149–177 μm | | 1.5 | | | 1.8 | | |
| | below 149 μm | | 8.8 | | | 42.7 | | |

(*)Classified by using a standard mesh screen in accordance with JIS Z 8801-1966.

EXAMPLE 1

185 g of ground product of each of the various cereals indicated in Table 5, 370 ml of water, 1.15 g (15.6 U/g of raw material as saccharifying power) of a saccharifying enzyme preparation A shown in Table 2 derived from Rhizopus sp. and 45 ml of yeast starter (Saccharomyces sp.; $1.2 \times 10^8$ cells/ml.) were mixed with stirring in 1 liter of Meyer flask, and fermentation was carried out at 25° C. for 120 hours. The results of fermentation are shown in Table 5.

TABLE 5

| Raw material | Degree of grinding (see Table 4) | Process of the invention | | | Conventional process[d] |
|---|---|---|---|---|---|
| | | pH | TA[a] (ml) | Alc[b] (%) | FE[c] (%) | FE (%) |
| Yellow dent maize | A | 4.8 | 3.1 | 14.5 | 88.3 | 87.2 |
| Sorghum | A | 4.7 | 3.5 | 14.5 | 88.1 | 87.3 |
| Barley | A | 4.8 | 3.5 | 13.7 | 88.0 | 86.8 |
| Wheat | A | 4.8 | 3.6 | 13.7 | 87.5 | 87.0 |
| Rye | A | 4.6 | 4.0 | 13.8 | 88.7 | 87.3 |
| Rice | A | 4.9 | 3.0 | 16.2 | 91.2 | 90.8 |
| German millet | B | 4.8 | 3.2 | 12.5 | 85.0 | 84.3 |
| Barnyard millet | B | 4.6 | 4.1 | 10.3 | 82.9 | 82.0 |
| Common millet | B | 4.9 | 3.0 | 12.1 | 85.9 | 84.2 |

[a]TA: total acidity, ml of N/10 NaOH required for neutralizing 10 ml of mash.
[b]Alc: alcohol content by volume
[c]FE: fermentation efficiency $= \dfrac{\text{Alcohol Produced (ml)}}{\text{Theoretical Alcohol (ml)}} \times 100(\%)$
[d]Conventional method: a conventional method in which the raw material was first cooked at a high temperature (150° C.) and thereafter saccharified and fermented.

EXAMPLE 2

140 g of a ground product of a germ-removed fraction of each of the cereals shown in Table 6, 0.28 g (5.0 U/g of raw material) of the saccharifying enzyme preparation A derived from Rhizopus sp. as shown in Table 2, 80 ml of water, 322 ml of stillage and 25 ml of a yeast starter ($1.1 \times 10^8$ cells/ml) were mixed with stirring, and fermentation was performed at 30° C. for 90 hours. The stillage used was obtained by subjecting the waste liquor discharged from the alcohol recovery tower to centrifugal separation to remove coarse solid components. The results are shown in Table 6.

TABLE 6

| Raw material | Degree of grinding (see Table 4) | Process of the invention | | | Conventional process |
|---|---|---|---|---|---|
| | | pH | TA (ml) | Alc (%) | FE (%) | FE (%) |
| Yellow dent maize | E | 4.8 | 3.8 | 11.8 | 90.0 | 88.2 |
| Sorghum | E | 4.7 | 3.7 | 11.8 | 89.5 | 88.0 |

TABLE 6-continued

| Raw material | Degree of grinding (see Table 4) | Process of the invention pH | TA (ml) | Alc (%) | FE (%) | Conventional process FE (%) |
|---|---|---|---|---|---|---|
| Barley | E | 4.7 | 3.7 | 11.6 | 88.7 | 87.1 |
| Wheat | E | 4.6 | 3.9 | 11.5 | 88.0 | 86.3 |
| Rye | E | 4.6 | 4.0 | 11.6 | 88.1 | 86.9 |
| Rice | E | 4.9 | 3.5 | 13.6 | 93.7 | 92.5 |

EXAMPLE 3

185 g of a whole grain product of white dent maize and Sorghum, 0.33 g (4 U/g of raw material) of the saccharifying enzyme B shown in Table 2 derived from Rhizopus sp., 80 mg of $K_2S_2O_5$, 370 ml of water and 25 ml of yeast starter ($1.2 \times 10^8$ cells/ml) were mixed with stirring, and fermentation was performed at 32° C. for 110 hours. The results are shown in Table 7.

TABLE 7

| Raw material | Degree of grinding (see Table 4) | Process of the invention pH | TA (ml) | Alc (%) | FE (%) | Conventional process FE (%) |
|---|---|---|---|---|---|---|
| White dent maize | E | 4.9 | 3.0 | 14.5 | 88.5 | 87.1 |
| Sorghum | E | 4.9 | 3.0 | 14.5 | 88.3 | 87.2 |

EXAMPLE 4

Four liters of yeast starter ($1.2 \times 10^8$ cell/ml) was put into a 100-liter fermentation tank. A whole grain ground product (the degree of grinding F) of sorghum and mashing liquor were mixed in a weight ratio of 1:2, and a saccharifying enzyme preparation D shown in Table 2 derived from Asp. sp. in an amount of 20 units per gram of sorghum as a saccharifying power was added to form a slurry. The slurry was gradually added so that the number of yeast cells in the mash after the addition was kept always at more than $2 \times 10^7$ cells/ml. The total amount of the mash was adjusted to 84 liters, and fermentation was carried out at 32° C. for 96 hours. The mashing liquor used in this experiment was a mixture of water and stillage in a ratio of 7:3 by volume. The stillage used was the one obtained by performing the same treatment as described in Example 2. The results are given in Table 8 which shows changes with time in the amount of direct reducing sugar in the mash, and in Table 9 which shows changes with time in the number of yeast cells in the mash and the results of fermentation.

TABLE 8

| Time (hours) from the start of addition of the raw material | Process of the invention | Conventional process |
|---|---|---|
| 1 | 1.10% | 6.79% |
| 10 | 1.65% | 6.45% |
| 24 | 0.17% | 2.52% |
| 48 | 0.14% | 0.18% |
| 72 | 0.12% | 0.12% |
| 96 | 0.09% | 0.10% |

TABLE 9

| Process of the invention | | | | | | | | | | | Conventional process |
|---|---|---|---|---|---|---|---|---|---|---|---|
| Number of yeast cells in the mash ($\times 10^7$ cells/ml) Time (hours) from the start of addition of the raw material | | | | | | | Results of fermentation | | | | |
| 1 | 5 | 10 | 24 | 48 | 72 | 96 | pH | TA (ml) | Alc (%) | FE (%) | FE (%) |
| 4.2 | 2.0 | 6.8 | 18 | 13 | 10 | 8 | 5.0 | 3.0 | 15.0 | 89.5 | 88.2 |

EXAMPLE 5

400 ml of yeast starter ($1.2 \times 10^8$ cells/ml) was put into a 10-liter glass fermentation tank (inside diameter 20 cm, height 40 cm). Each of the various materials in the ground state shown in Table 10 and mashing liquor were mixed in a weight ratio of 1:2, and 23 units, as a saccharifying power, per gram of the raw material of the saccharifying enzyme preparation D shown in Table 2 derived from Asp. sp. was added to prepare a slurry. The slurry was gradually added so that the number of yeast cells in the mash after the addition was always kept at more than $2 \times 20^7$ cells/ml. The total amount of the mash was adjusted to 8.4 liters, and fermentation was carried out at 35° C. for 110 hours. The mashing liquor used in this experiment was a mixture of water and stillage in a ratio of 1:1, and the stillage was the one obtained by performing the same treatment as in Example 2.

The results are shown in Table 10.

TABLE 10

| Raw material | Degree of grinding (see Table 4) | Process of the invention Number of yeast cells ($\times 10^7$ cells/ml in the mash) Time (hours) from the start of addition of the raw material | | | | Results of fermentation | | | | Conventional process |
|---|---|---|---|---|---|---|---|---|---|---|
| | | 1 | 5 | 10 | 24 | pH | TA (ml) | Alc (%) | FE (%) | FE (%) |
| Maize | B | 4.0 | 2.2 | 6.0 | 18 | 4.9 | 3.8 | 14.4 | 88.1 | 87.6 |
| Sorghum | B | 4.5 | 2.0 | 5.9 | 18 | 4.7 | 4.0 | 14.4 | 87.8 | 87.5 |
| Barley | B | 5.0 | 2.9 | 7.8 | 21 | 4.9 | 3.5 | 14.1 | 87.6 | 86.5 |
| Wheat | E | 4.8 | 2.6 | 6.2 | 17 | 4.8 | 3.7 | 14.1 | 87.4 | 86.8 |
| Rye | E | 4.7 | 2.4 | 7.0 | 18 | 4.6 | 4.1 | 14.2 | 88.0 | 87.1 |
| Rice | E | 3.5 | 3.7 | 6.9 | 20 | 5.0 | 3.5 | 16.5 | 90.5 | 90.2 |
| German millet | E | 6.0 | 4.2 | 8.0 | 18 | 4.7 | 3.9 | 12.9 | 84.7 | 83.6 |
| Barnyard millet | E | 5.0 | 2.8 | 6.1 | 17 | 4.7 | 4.5 | 10.6 | 82.5 | 81.5 |
| Common millet | E | 4.5 | 2.1 | 6.1 | 19 | 4.9 | 3.9 | 12.4 | 86.0 | 84.9 |

EXAMPLE 6

400 ml of yeast starter ($1.1 \times 10^8$ cells/ml) was put into a 10-liter glass fermentation tank (inside diameter 20 cm, height 40 cm). A ground product of each of the raw materials shown in Table 11 and mashing liquor were mixed in a weight ratio of 1:1.8, and 4 units, as a saccharifying power, per g of the raw material of the saccharifying enzyme preparation E shown in Table 2 derived from Asp. sp. was added to form a slurry. The slurry was gradually added so that the number of yeast cells in the mash after the addition was always kept at more than $2 \times 10^7$ cells/ml. The total amount of the mash was adjusted to 8.4 liters, and fermentation was carried out at 32° C. for 120 hours. The mashing liquor used in this experiment was a mixture of water and stillage in a ratio of 8:2. The stillage was the one obtained by performing the same treatment as in Example 2.

The results are shown in Table 11.

TABLE 11

| | | The process of the invention | | | | | | | Conventional process |
|---|---|---|---|---|---|---|---|---|---|
| | Degree of grinding | Number of yeast cells ($\times 10^7$ cells/ml in the mash) Time (hours) after the start of addition of the raw material | | | | Results of fermentation | | | |
| Raw material | (see Table 4) | 1 | 5 | 10 | 24 | pH | TA (ml) | Alc (%) | FE (%) | FE (%) |
| Maize | G | 4.5 | 4.0 | 7.2 | 19 | 4.9 | 3.7 | 15.3 | 87.5 | 87.7 |
| Sorghum | G | 4.7 | 3.1 | 6.0 | 17 | 4.8 | 3.2 | 15.6 | 87.6 | 87.3 |
| Rice | G | 3.8 | 3.0 | 7.8 | 18 | 4.9 | 3.4 | 17.1 | 89.7 | 89.5 |

EXAMPLE 7

120 g of a starch fraction separated from each of the raw materials shown in Table 12, 1.34 g (25 U/g of raw material) of the saccharifying enzyme preparation B shown in Table 2 derived from Rhizopus sp., 408 ml of stillage, and 25 ml of yeast starter were mixed with stirring, and fermentation was carried out at 35° C. for 96 hours. The stillage used in this experiment was the liquid discharged from the alcohol recovery tower. The results are shown in Table 12.

TABLE 12

| | Process of the invention | | | | Conventional process |
|---|---|---|---|---|---|
| Raw material | pH | TA (ml) | Alc (%) | FE (%) | FE (%) |
| Maize | 4.5 | 4.0 | 12.3 | 90.0 | 87.7 |
| Sorghum | 4.4 | 4.1 | 12.3 | 89.5 | 88.0 |
| Barley | 4.4 | 4.2 | 12.2 | 88.6 | 87.9 |
| Wheat | 4.3 | 4.3 | 12.2 | 88.5 | 87.0 |
| Rye | 4.2 | 4.3 | 12.3 | 89.1 | 88.3 |
| Rice | 4.7 | 4.1 | 12.5 | 92.1 | 90.0 |
| Sweet potato | 4.3 | 4.0 | 12.3 | 89.2 | 86.8 |
| Cassava | 4.2 | 4.2 | 12.3 | 89.5 | 88.5 |

EXAMPLE 8

1540 g of a whole grain ground product (the degree of grinding E) of yellow dent maize, 1260 g of commercial corn starch, 10.5 g (8.4 U/g of raw material) of saccharifying enzyme preparation derived from Rhizopus sp. (B in Table 2), 5.6 liters of water and 2.4 liters of stillage and 500 ml of yeast starter ($1.0 \times 10^8$ cells/ml) were mixed, and fermentation was carried out for 100 hours at 32° C. The results are shown in Table 13.

TABLE 13

| | Process of the invention | | | | Conventional process |
|---|---|---|---|---|---|
| Raw material | pH | TA (ml) | Alc (%) | FE (%) | FE (%) |
| Yellow dent maize and commercial corn starch | 4.6 | 6.1 | 12.2 | 88.0 | 87.1 |

EXAMPLE 9

126 g of a whole grain ground product (the degree of grinding B) of yellow dent maize, 14 g (4.6 U/g of raw material) of ground malt (A shown in Table 3), 0.22 g (3.5 U/g of raw material) of saccharifying enzyme preparation from Rhizopus sp. (B in Table 2), 80 mg of $K_2S_2O_5$, 402 ml of water and 25 ml of yeast starter ($1.1 \times 10^8$ cells/ml) mixed with stirring, and fermentation was carried out at 30° C. for 96 hours. The results are shown in Table 14.

TABLE 14

| | Process of the invention | | | | Conventional process |
|---|---|---|---|---|---|
| Raw material | pH | TA (ml) | Alc (%) | FE (%) | FE (%) |
| Yellow dent maize and malt | 4.7 | 3.0 | 11.2 | 88.2 | 87.3 |

EXAMPLE 10

670 ml of yeast starter ($1.0 \times 10^8$ cells/ml) was put into a 10-liter glass fermentation tank (inside diameter 20 cm, height 40 cm). Ground maize, ground malt (B in Table 3; 22 U/g of raw material as saccharifying power), and mashing liquor were mixed in a weight ratio (maize:malt:mashing liquor) or 4:1:14.5, and 320 ppm of $K_2S_2O_5$ was added to form a slurry. The slurry was gradually added so that the number of yeast cells in the mash after the addition was kept always at more than $2 \times 10^7$ cells/ml. The total amount of the mash was adjusted to 8.7 liters, and fermentation was carried out at 32° C. for 96 hours.

The mashing liquor used in this experiment was a mixture of water and stillage in a ratio of 7:3. The results are shown in Table 15.

TABLE 15

| | | Process of the invention | | | | | | | | | | Conventional process |
|---|---|---|---|---|---|---|---|---|---|---|---|---|
| | Degree of grinding | Number of the yeast cells in the mash ($\times 10^7$ cells/ml) Time (hours) after the start of addition of the raw material | | | | | | | Results of fermentation | | | |
| Raw material | (see Table 4) | 1 | 5 | 10 | 24 | 48 | 72 | 96 | pH | TA (ml) | Alc (%) | FE (%) | FE (%) |
| Maize and malt | B | 4.0 | 2.4 | 6.0 | 19 | 15 | 7.2 | 5 | 4.8 | 3.0 | 10.5 | 87.3 | 86.8 |

A similar experiment to the above was carried out using sorghum, barley, wheat, rye and rice. The results are shown in Table 16.

TABLE 16

| Raw material | Degree of grinding (see Table 4) | Process of the invention Number of yeast cells in the mash ($\times 10^7$ cells/ml) Time (hours) from the start of addition of the raw material | | | | | Results of fermentation | | | Conventional process |
|---|---|---|---|---|---|---|---|---|---|---|
| | | 1 | 5 | 10 | 24 | pH | TA (ml) | Alc (%) | FE (%) | FE (%) |
| Sorghum and malt | B | 3.8 | 2.0 | 5.8 | 18 | 5.0 | 3.2 | 10.6 | 87.0 | 87.0 |
| Barley and malt | C | 5.0 | 2.8 | 7.0 | 19 | 4.9 | 3.1 | 10.5 | 87.2 | 86.5 |
| Wheat and malt | E | 4.6 | 2.2 | 6.4 | 19 | 4.9 | 3.0 | 10.5 | 87.1 | 87.0 |
| Rye and malt | E | 4.5 | 2.1 | 6.5 | 17 | 4.9 | 3.3 | 10.6 | 88.0 | 87.5 |
| Rice and malt | C | 5.6 | 2.7 | 7.5 | 20 | 4.9 | 3.0 | 11.9 | 89.7 | 89.0 |

EXAMPLE 11

800 ml of yeast starter ($1.3 \times 10^8$ cells/ml) was put into a 10-liter glass fermentation tank (inside diameter 20 cm, height 40 cm).

A ground product of each of the raw materials shown in Table 17 ground malt (C in Table 3; 11.6 U/g of raw material was saccharifying power) and water were mixed in a weight ratio of 8.7:1:22.8 (a ground product:ground malt:water) and 160 ppm of $K_2S_2O_5$ was further added to form a slurry.

The slurry was gradually added to the tank so that the number of yeast cells in the mash after the addition was kept always at more than $2 \times 10^7$ cells/ml. The total amount of the mash was adjusted to 8.8 liters, and fermentation was carried out at 28° C. for 120 hours. The results are shown in Table 17.

TABLE 17

| Raw material | Degree of grinding (see Table 4) | Process of the invention | | | | Conventional process |
|---|---|---|---|---|---|---|
| | | pH | TA (ml) | Alc (%) | FE (%) | FE (%) |
| Maize and malt | G | 4.6 | 3.5 | 11.7 | 86.5 | 86.6 |
| Sorghum and malt | G | 4.5 | 4.0 | 11.9 | 86.8 | 86.5 |
| Rice and malt | G | 4.8 | 4.1 | 12.9 | 87.5 | 87.3 |

EXAMPLE 12

185 g of ground cassava (dried), 370 ml of water, 200 ml of stillage, 0.58 g (7.8 U/g of raw material) of the saccharifying enzyme preparation derived from Rhizopus sp. (A in Table 2), 45 ml of yeast starter ($1.2 \times 10^8$ cells/ml) were mixed with stirring, and fermentation was carried out at 30° C. for 96 hours. The results are shown in Table 18.

TABLE 18

| Degree of grinding (see Table 4) | Process of the invention | | | | Conventional process |
|---|---|---|---|---|---|
| | pH | TA (ml) | Alc (%) | FE (%) | FE (%) |
| B | 4.2 | 3.1 | 12.5 | 87.8 | 88.2 |
| D | 4.3 | 3.3 | 12.6 | 88.3 | 88.4 |
| E | 4.3 | 3.1 | 12.7 | 89.6 | 88.5 |

EXAMPLE 13

185 g of ground sweet potato (dried chips), 305 ml of water, 165 ml of stillage, 0.32 g (3.9 U/g of raw material) of the saccharifying enzyme derived from Rhizopus sp. (B in Table 2), and 40 ml ($1.0 \times 10^8$ cells/ml) of yeast starter were mixed with stirring, and fermentation was carried out at 32° C. for 120 hours. The results are shown in Table 19.

TABLE 19

| Degree of grinding (see Table 4) | Process of the invention | | | | Conventional process |
|---|---|---|---|---|---|
| | pH | TA (ml) | Alc (%) | FE (%) | FE (%) |
| B | 4.5 | 4.1 | 12.2 | 91.2 | 91.8 |
| E | 4.6 | 4.0 | 12.3 | 92.0 | 91.5 |

EXAMPLE 14

112 g of a ground product of each of the raw materials (dried) shown in Table 20, 28 g of ground malt (B in Table 3; 22 U/g of raw material), 200 ml of water, 200 ml of stillage, 320 mg of $K_2S_2O_5$, and 25 ml ($1.3 \times 10^8$ cells/ml) of yeast starter were mixed, and fermentation was carried out at 28° C. for 120 hours. The results are shown in Table 20.

TABLE 20

| Raw material | Degree of grinding (see Table 4) | Process of the invention | | | | Conventional process |
|---|---|---|---|---|---|---|
| | | pH | TA (ml) | Alc (%) | FE (%) | FE (%) |
| Cassava and malt | E | 4.3 | 2.4 | 12.6 | 87.8 | 86.8 |
| Sweet potato and malt | E | 4.5 | 4.3 | 11.1 | 90.2 | 90.6 |

EXAMPLE 15

400 ml of yeast starter ($1.3 \times 10^8$ cells/ml) was put into a 10-liter glass fermentation tank (inside diameter 20 cm, height 40 cm).

Separately, a ground product of germ-removed fraction of each of the cereals shown in Table 21 and mashing liquor were mixed in a weight ratio of 1:2.5, and the enzyme preparation derived from a microorganism (C in Table 2; 5.9 U/g of raw material) was added to form a slurry. The slurry was then added gradually to the tank so that the number of yeast cells in the mash after the addition was kept always at more than $2 \times 10^7$ cells/ml. The total amount of the mash was adjusted to 7.6 liters, and fermentation was carried out at 30° C. for 120 hours. The liquor used in this experiment was a mixture of water and stillage in a ratio of 1:1. The results are shown in Table 21.

TABLE 21

| Raw material | Degree of grinding (see Table 4) | Process of the invention | | | | | | | | Conventional process |
|---|---|---|---|---|---|---|---|---|---|---|
| | | Number of yeast cells in the mash (× 10⁷ cells/ml) Time (hours) after the start of addition of the raw material | | | | | Results of fermentation | | | FE (%) |
| | | 1 | 5 | 10 | 24 | pH | TA (ml) | Alc (%) | FE (%) | |
| Maize | G | 6.8 | 4.2 | 8.3 | 19 | 4.8 | 3.6 | 12.8 | 88.0 | 87.0 |
| Sorghum | E | 6.2 | 2.1 | 7.1 | 17 | 4.9 | 3.5 | 12.9 | 88.1 | 87.9 |
| Rice | G | 7.1 | 4.5 | 7.8 | 20 | 5.0 | 3.2 | 14.7 | 92.7 | 92.2 |

What is claimed is:

1. A process for producing a fermented mash containing from 12.2 to 17.1 V/V% of alcohol, which comprises mixing at least one non-heated raw cereal with a mashing liquor in a weight ratio (weight of said raw cereal: weight of mashing liquor) of from 1:3.4 to 1:1.8 to form a slurry; thereafter without heating the slurry, without adjusting the pH of the slurry and without adding liquefying enzyme, adding a saccharifying enzyme preparation derived from a microorganism source in an amount of at least 3.5 units of saccharifying titer per gram of said raw cereal on a wet basis to the slurry, adding an alcoholic fermenting yeast having an initial concentration of at least $2 \times 10^7$ cells/ml of slurry, and fermenting the slurry at a pH of from 4.0 to 5.0, at a temperature of 25° to 35° C. for 90 to 120 hours.

2. The process of claim 1, wherein the raw cereal is selected from the group consisting of maize, sorghum, wheat, barley, rye, rice, barnyard millet, German millet and common millet.

3. The process of claim 1, wherein the mashing liquor is water, or a mixture of water and distillers stillage.

4. The process of claim 3, wherein the mashing liquor is completely substituted by the distillers stillage.

5. The process of claim 1, wherein the enzyme preparation is derived from a microorganism of the genus Rhizopus.

6. The process of claim 1, wherein the saccharifying titer of the enzyme preparation is 3.5 to 25 units.

7. The process of claim 1, further comprising adding less than 320 ppm of sulfur dioxide to the slurry.

8. The process according to claim 1, wherein at least 30% of the raw cereal has a particle size not exceeding 840 μm.

9. A process for producing a fermented mash containing from 12.2 to 17.1 V/V% of alcohol, which comprises mixing at least one non-heated raw cereal and ground malt with a mashing liquor in a weight ratio (weight of said raw cereal including malt: wieght of mashing liquor) of from 1:3.4 to 1:1.8 to form a slurry; thereafter without heating the slurry, without adjusting the pH of the slurry and without adding liquefying enzyme, adding a saccharifying enzyme preparation derived from a microorganism source wherein the total saccharifying power of the malt and enzyme preparation based on units of the saccharifying titer of the enzyme preparation is at least 3.5 units, adding an alcoholic fermenting yeast having an initial concentration of at least $2 \times 10^7$ cells/ml of slurry, and fermenting the slurry at a pH of from 4.0 to 5.0, at a temperature of from 25° to 35° C. for 90 to 120 hours.

10. The process of claim 9, wherein the raw cereal is selected from the group consisting of maize, sorghum, barley, wheat, rye, rice, barnyard millet, German millet and common millet.

11. The process of claim 9, wherein the mashing liquor is water, or a mixture of water and distillers stillage.

12. The process of claim 11, wherein the mashing liquor is completely substituted by the distillers stillage.

13. The process of claim 9, wherein the enzyme preparation is derived from a microorganism of the genus Rhizopus.

14. The process of claim 9, wherein the saccharifying titer of the enzyme preparation is 0.3 to 10 units.

15. The process of claim 9, further comprising adding less than 320 ppm of sulfur dioxide to the slurry.

16. The process according to claim 9, wherein at least 30% of the raw cereal has a particle size not exceeding 840 μm.

17. A process for producing a fermented mash containing from 12.2 to 17.1 V/V% of alcohol, which comprises mixing at least one non-heated raw cereal and ground malt with a mashing liquor in a weight ratio (weight of said raw cereal including malt: weight of mashing liquor) of from 1:3.4 to 1:1.8 to form a slurry, the amount of malt being sufficient to provide at least 10 units of saccharifying power per gram of said raw cereal; thereafter without heating the slurry, without adjusting the pH of the slurry and without adding liquefying enzyme, adding an alcoholic fermenting yeast having an initial concentration of at least $2 \times 10^7$ cells/ml of slurry, and ferementing the slurry at a pH of from 4.0 to 5.0, at a temperature of 25° to 35° C. for 90 to 120 hours.

18. The process of claim 17, wherein the raw cereal is selected from the group consisting of maize, sorghum, barley, rye, rice, barnyard millet, German millet and common millet.

19. The process of claim 17, wherein the mashing liquor is water, or a mixture of water and distillers stillage.

20. The process of claim 19, wherein the mashing liquor is completely substituted by the distillers stillage.

21. The process of claim 17, wherein the amount of malt is sufficient to provide from 10 to 25 units of saccharifying power per gram of starchy material.

22. The process of claim 17, further comprising adding less than 320 ppm of sulfer dioxide to the slurry.

23. The process according to claim 17, wherein at least 30% of the raw cereal has a particle size not exceeding 840 μm.

24. A process for producing a fermented mash containing from 12.2 to 17.1 V/V% of alcohol, which comprises mixing at least one non-heated raw cereal with a mashing liquor in a weight ratio (weight of said raw cereal: weight of mashing liquor) of from 1:3.4 to 1:1.8 to form a slurry; thereafter without heating the slurry, without adjusting the pH of the slurry and without adding liquefying enzyme, adding a saccharifying enzyme preparation derived from a microorganism source having at least 3.5 units of saccharifying titer per gram of said raw cereal on a wet basis to the slurry, and mixing part of the slurry with yeast to provide a yeast population of at least $2 \times 10^7$ cells/ml of the slurry and then adding gradually the remainder of the slurry to the yeast containing slurry so that the yeast population in the slurry is always in the amount of at least $2 \times 10^7$ cells/ml, and fermenting the slurry at a pH of from 4.0 to 5.0, at a temperature of 25° to 35° C. for 90 to 120 hours.

25. The process according to claim 24, wherein at least 30% of the raw cereal has a particle size not exceeding 840 μm.

26. A process for producing a fermented mash containing from 12.2 to 17.1 V/V% of alcohol, which comprises mixing at least one non-heated raw cereal and ground malt with a mashing liquor in a weight ratio (weight of said raw cereal including malt: weight of mashing liquor) of from 1:3.4 to 1:1.8 to form a slurry; thereafter without heating the slurry, without adjusting the pH of the slurry and without adding liquefying enzyme, adding a saccharifying enzyme preparation derived from a microorganism source wherein the total saccharifying power of the malt and enzyme preparation based on units of the saccharifying titer of the enzyme preparation is at least 3.5 units and mixing part of the slurry with yeast to provide a yeast population of at least $2 \times 10^7$ cells/ml of the slurry and then adding gradually the remainder of the slurry to the yeast containing slurry so that the yeast population in the resulting slurry is always in the amount of at least $2 \times 10^7$ cells/ml, and fermenting the slurry at a pH of from 4.0 to 5.0, at a temperature of 25° to 35° C. for 90 to 120 hours.

27. The process according to claim 26, wherein at least 30% of the raw cereal has a particle size not exceeding 840 μm.

28. A process for producing a fermented mash containing from 12.2 to 17.1 V/V% of alcohol, which comprises mixing at least one non-heated raw cereal and ground malt with a mashing liquor in a weight ratio (weight of said raw cereal including malt: weight of mashing liquor) of from 1:3.4 to 1:1.8 to form a slurry, the amount of malt being sufficient to provide at least 10 units of saccharifying power per gram of said raw cereal; thereafter without heating the slurry, without adjusting the pH of the slurry and without adding liquefying enzyme, mixing part of the slurry with yeast to provide a yeast population of at least $2 \times 10^7$ cells/ml of the slurry and then adding gradually the remainder of the slurry to the yeast containing slurry so that the yeast population in the resulting slurry is always in the amount of at least $2 \times 10^7$ cells/ml, and fermenting the slurry at a pH of from 4.0 to 5.0, at a temperature of 25° to 35° C. for 90 to 120 hours.

29. The process according to claim 28, wherein at least 30% of the raw cereal has a particle size not exceeding 840 μm.

30. A process for producing a fermented mash containing from 12.2 to 17.1 V/V% of alcohol, which comprises mixing at least one non-heated ground raw cereal with a mashing liquor which contains 50 to 100% of distillers stillage in a weight ratio (weight of said raw cereal: weight of mashing liquor) of from 1:3.4 to 1:1.8 to form a slurry; thereafter without heating the slurry, without adjusting the pH of the slurry, and without adding liquefying enzyme, adding a saccharifying enzyme preparation derived from a microorganism source in an amount of at least 3.5 units of saccharifying titer per gram of said raw cereal on a wet basis to the slurry, adding an alcoholic fermenting yeast having an initial concentration of at least $2 \times 10^7$ cells/ml of slurry and fermenting the slurry at a pH of from 4.0 to 5.0 at a temperature of 25° to 35° C. and from 90 to 120 hours.

31. The process of claim 30, wherein the raw cereal is selected from the group consisting of maize, sorghum, wheat, barley, rye, rice, barnyard millet, German millet and common millet.

32. The process of claim 30, wherein the enzyme preparation is derived from a microorganism of the genus Rhizopus.

33. The process of claim 30, wherein the saccharifying titer of the enzyme preparation is 3.5 to 25 units.

34. The process of claim 30, further comprising adding less than 320 ppm of sulful dioxide to the slurry.

* * * * *